(12) United States Patent
Wurtz (10) Patent No.: US 6,704,428 B1
(45) Date of Patent: Mar. 9, 2004

(54) AUTOMATIC TURN-ON AND TURN-OFF CONTROL FOR BATTERY-POWERED HEADSETS

(76) Inventor: Michael Wurtz, 1156 Laurel Ave., St. Paul, MN (US) 55104

( * ) Notice: Subject to any disclaimer, the term of this patent is extended or adjusted under 35 U.S.C. 154(b) by 0 days.

(21) Appl. No.: 09/518,917

(22) Filed: Mar. 6, 2000

Related U.S. Application Data (60) Provisional application No. 60/123,150, filed on Mar. 5, 1999.

(51) Int. Cl.[7] ............................................. H04R 25/00
(52) U.S. Cl. ...................... 381/370; 381/384; 381/71.9; 381/74
(58) Field of Search .................... 381/182, 370–375, 381/315, 365, 312, 323, 327, 71.6, 71.7, 71.9, 71.13, 71.14, 71.19, 72, 74

(56) References Cited

U.S. PATENT DOCUMENTS

| | | | | |
|---|---|---|---|---|
| 3,227,836 A | * | 1/1966 | Renwick | 200/61.58 R |
| 4,010,340 A | * | 3/1977 | Palmaer | 200/332 |
| 4,160,135 A | * | 7/1979 | Gorike | 381/372 |
| 4,473,906 A | * | 9/1984 | Warnaka et al. | 367/1 |
| 4,494,074 A | | 1/1985 | Bose | 330/109 |
| 4,654,871 A | * | 3/1987 | Chaplin et al. | 128/848 |
| 4,747,145 A | | 5/1988 | Wiegel | 381/183 |
| 4,833,719 A | * | 5/1989 | Carme et al. | 381/71.6 |
| 4,922,542 A | | 5/1990 | Sapiejewski | 381/187 |
| 4,955,729 A | * | 9/1990 | Marx | 381/322 |
| 5,091,954 A | * | 2/1992 | Sasaki et al. | 381/71.12 |
| 5,101,504 A | * | 3/1992 | Lenz | 200/52 R |
| 5,144,678 A | * | 9/1992 | Lenz | 381/371 |
| 5,181,252 A | | 1/1993 | Sapiejewski et al. | 381/187 |
| 5,182,774 A | | 1/1993 | Bourk | 381/71 |
| 5,343,523 A | * | 8/1994 | Bartlett et al. | 379/395 |
| 5,463,428 A | * | 10/1995 | Lipton et al. | 349/13 |
| 5,635,948 A | * | 6/1997 | Tonosaki | 345/156 |
| 5,675,658 A | * | 10/1997 | Brittain | 381/186 |
| 5,708,725 A | * | 1/1998 | Ito | 381/370 |
| 5,732,143 A | * | 3/1998 | Andrea et al. | 381/71.13 |
| 5,825,897 A | * | 10/1998 | Andrea et al. | 381/71.13 |
| 6,069,959 A | * | 5/2000 | Jones | 330/262 |
| 6,118,878 A | * | 9/2000 | Jones | 381/71.11 |
| 6,130,953 A | * | 10/2000 | Wilton et al. | 379/430 |
| 6,278,786 B1 | * | 8/2001 | McIntosh | 381/71.13 |

OTHER PUBLICATIONS

"User Instructions, ANR–1D, Active Noise Reduction Headset", *TELEX Communications, Inc.,* Minneapolis, MN, (1999), pp. 1–9.

"ANR 101 Section 1: The Basics of ANR", *LightSPEED Aviation, Inc.,* http://www.lightspeed.com, pp. 1–6, (2000).

"ANR 101, A Tutorial on Active Noise Reduction", *LightSPEED Aviation, Inc.,* http://www.lightspeed.com, pp. 1–2, (2000).

Busch, M., "AVweb Product Report: LightSPEED Technologies 25XL Active Noise Reduction Headset", file:// C:\TMP\%20LightSPEED%2025XL%20ANR%20Headset.htm, pp. 1–7, (1997).

* cited by examiner

*Primary Examiner*—Curtis Kuntz
*Assistant Examiner*—P. Dabney
(74) *Attorney, Agent, or Firm*—Schwegman, Lundberg, Woessner & Kluth, P.A.

(57) ABSTRACT

Some workers wear headsets to protect their hearing from loud persistent noises, such as airplane engines and construction equipment. These headsets are generally passive or active, with the active ones including ear speakers and automatic noise-reduction (ANR) circuitry to cancel or suppress certain types of loud persistent noises. One problem with active headsets, particulary those that are battery-powered, concerns battery life. Workers often take the headset off or store them without turning them off and thus wasting costly battery life. Accordingly, the inventor devised active headsets with automatic turn-on and/or turn-off circuits. One exemplary embodiment senses a condition of the headsets, for example, the light, pressure, or temperature within one earcup, and then turns the headset on or off in response to the sensed condition.

13 Claims, 6 Drawing Sheets

AUTOMATIC TURN-ON AND TURN-OFF CONTROL FOR BATTERY-POWERED HEADSETS

CROSS-REFERENCE TO RELATED APPLICATION

This patent application is a continuation of U.S. provisional patent application No. 60/123,150 filed Mar. 5, 1999. This application is incorporated herein by reference.

TECHNICAL FIELD

The present invention concerns headphones or headsets, particularly battery-powered headsets with automatic noise-reduction circuitry.

BACKGROUND OF THE INVENTION

Headsets typically include two earcups which are worn over ears of users to enhance or protect their hearing. For example, many workers wear headsets to protect their hearing from loud persistent noises, such as airplane engines and construction equipment. These headsets are generally passive or active. Those that are passive only cover the ears with a sound-muffling material, whereas those that are active include ear speakers and automatic noise-reduction (ANR) circuitry. The noise-reduction circuitry automatically cancels or suppresses certain types of loud persistent noises. Active headsets are often battery-powered and include an on-off switch to turn them on and off.

One problem with battery-powered headsets, particularly those with automatic noise-reduction circuitry, concerns battery life. Workers having these headsets generally put on and take off their headphones many times throughout a workday, often forgetting to turn them off and wasting costly battery life. Moreover, for those headsets that are used infrequently with long storage times between uses, the turn-off problem is worse not only because their batteries are more apt to die, but fresh batteries are too often unavailable or inconvenient to obtain.

SUMMARY OF INVENTION

To address this and other needs, the inventor devised active headsets with automatic turn-on and/or turn-off circuits and related mode-control methods for active headsets. One exemplary embodiment senses a condition of the headsets, for example, the light, pressure, or temperature within one earcup, and then turns the headset on or off in response to the sensed condition. Other embodiments that include automatic noise-reduction (ANR) circuitry use an ANR driver to sense engagement of an earcup with a user's head and an ANR microphone to sense disengagement of the earcup from the user's head.

DETAILED DESCRIPTION OF THE PREFERRED EMBODIMENTS

The following detailed description, which references and incorporates FIGS. 1–6, describes and illustrates one or more specific embodiments of the invention. These embodiments, offered not to limit but only to exemplify and teach, are shown and described in sufficient detail to enable those skilled in the art to implement or practice the invention. Thus, where appropriate to avoid obscuring the invention, the description may omit certain information known to those of skill in the art.

Figure 1:
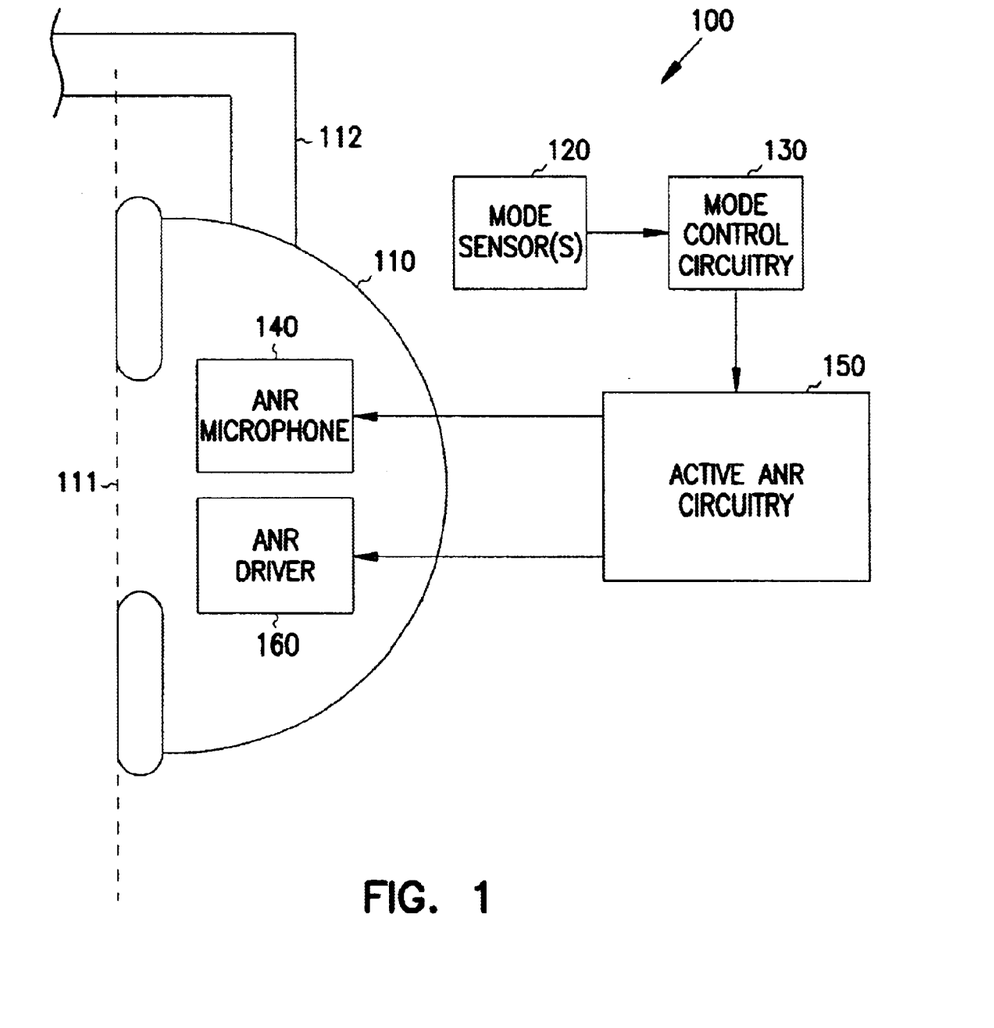
FIG. 1 is a block diagram of a first exemplary headset 100 incorporating the present invention.

FIG. 1 shows a first exemplary embodiment of an active, automatic-noise-reduction (ANR) headset 100 incorporating an automatic mode control feature in accord with the present invention. Headset 100 includes an earcup 110 attached to a bridge member 112. Earcup 110 fits over an ear and against the head of a user, represented generally as surface 111 in the FIG. (For simplicity, the figure omits a second earcup.) Headset 100 also includes a mode sensor 120, and a mode-control circuit 130, an ANR sensor or microphone 140, ANR circuitry 150, and an ANR driver 160. (ANR circuitry 150 includes one or more batteries and a power supply which are not shown.) (In some embodiments, the ANR function is implemented digitally.)

In operation, mode sensor 120, which is shown in broken form to emphasize that its placement can be virtually anywhere in or on the headset, senses a condition of earcup 110 (or more generally headset 100) and outputs a corresponding electrical signal to mode-control circuit 130. Mode-control circuit 130 processes the electrical signal, either switching the headset from a first operating mode to a second operating mode or leaving the headset in its current operating mode (or state.) For example, if the signal indicates that the earcup has been disengaged from the head of the user, mode-control circuit 130 deactivates ANR circuitry 150 or otherwise puts it in a standby mode to reduce power consumption.

However, if the signal indicates that the earcup has been engaged with the head of the user, mode-control circuit 120 enables or activates ANR circuitry 140 to control or otherwise affect the perceived acoustic energy within earcup 110. This generally entails ANR sensor 140 outputting an electrical signal representative of acoustic energy within earcup 110 to the ANR circuitry. In turn, the ANR circuitry processes the electrical signal and outputs a responsive electrical signal to ANR driver 140. ANR driver 140 ultimately produces an acoustic signal intended to cancel, suppress, or otherwise alter the acoustic energy within earcup 110.

In some variants of this first embodiment, the sensor comprises one or more mechanical switches, photo-sensors, temperature sensors, or pressure sensors. As used herein, light or photoelectric sensor includes any electrical or electromechanical device or component with useful photon-sensitive characteristics, coupled for use as a sensor. Temperature sensor includes any electrical device or component with useful temperature-dependent characteristics, coupled for use as a sensor. Pressure sensor includes any electrical or electromechanical device or component with useful pressure-dependent characteristics, coupled for use as a sensor.

In some mechanical variants, a normally open or normally closed mechanical switch closes or opens on sufficient deflection of at least a portion of the earcup, such as an ear cushion, or deflection of a bridge between two earcups, upon engagement or disengagement of the headset with the head of the user (head surface or more generally user surface). Engagement or disengagement makes or breaks a normally open or normally closed electrical contact which in turn operates a switch (not shown) between a power supply and the ANR circuitry.

In some photo-sensing variants, the photo-sensors sense light or temperature levels or changing light or temperature levels within or without the earcup. For photo sensors within the earcup or for photo sensor on other interior (head-confronting) surfaces of the headset (such as a bridge between two earcups), engagement of the headset generally reduces the sensed light and disengagement generally increases the sensed light.

Some temperature-sensing variants place the temperature sensors the head of the user, for example within the earcup on the bridge member. Thus, the sensors generally see increases in temperature upon engagement of the headsets and decreases upon disengagement.

It is also contemplated that some photo-sensing or temperature-sensing variants would facilitate automatically changing operational modes as a user wearing a headset moves between indoor and outdoor environments or between two indoor environments. For example, one can tune the sensors and/or mode control circuit to distinguish indoor environments from outdoor environments, correlate the distinction to the intended use of the headset, and switch the headset on or off or otherwise change the acoustic control function of the headset.

Figure 2:
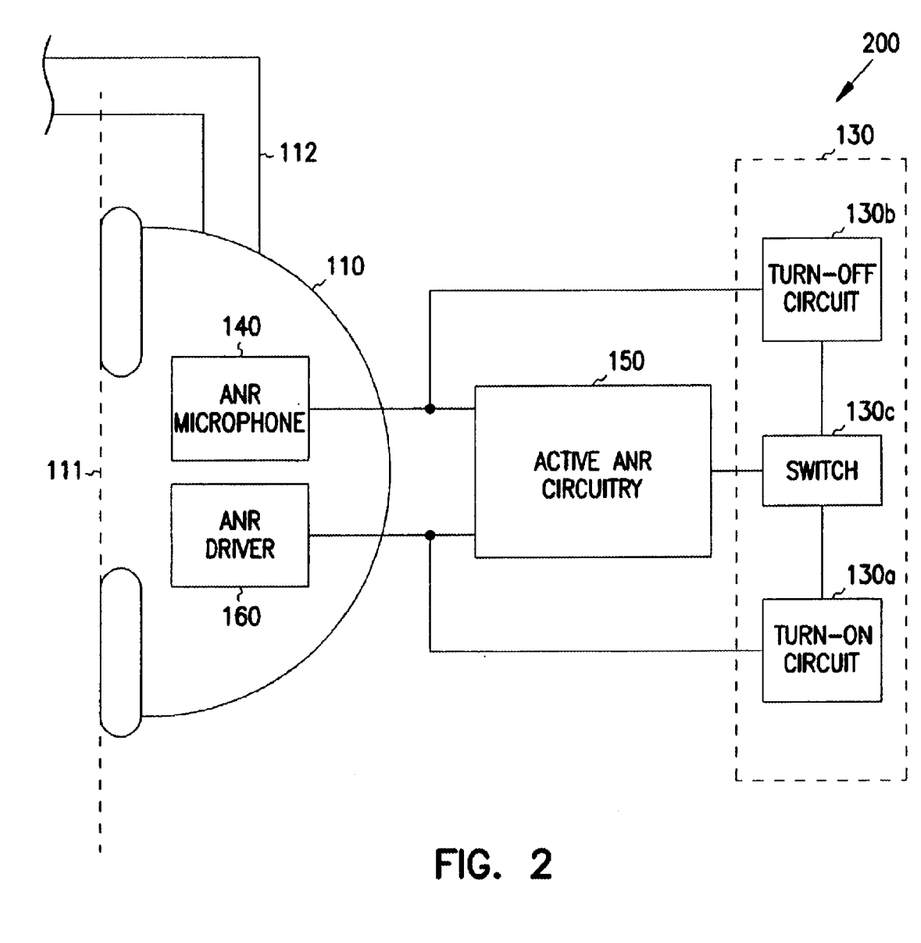
FIG. 2 is a block diagram of a second exemplary headset 200 incorporating the present invention.

FIG. 2 shows a second exemplary embodiment of an ANR headset 200 including an automatic mode control feature in accord with the invention. (FIG. 2 omits earcups for clarity.) Headset 200 includes an ANR microphone 140, ANR circuitry 150, an ANR driver 160, and implements automatic mode control using a turn-off circuit 130a, a turn-off circuit 130b, and a power switch 130c. Turn-off circuit 130 a is responsive to signals from ANR microphone 140 to control power switch 130c, and turn-on circuit 130b is responsive to signals from ANR driver 160 to control the power switch. Thus, unlike headset 100 in the first exemplary embodiment, headset 200 omits a dedicated mode sensor, and instead uses ANR driver 160 and microphone 140 as respective headset engagement and headset disengagement sensors.

More specifically, engaging earcup 110 with the head of a user generally results in an appreciable mechanical deflection of ANR driver 150, which responsively outputs an appreciable electrical signal to turn-on circuitry 130a. If the signal exceeds a threshold, turn-on circuitry 130a activates power switch 130c, thereby providing power to ANR circuitry 150.

On the other hand, after engagement, the earcup and surface 111 define a substantially closed volume that changes with user movements, such as head and jaw movements and the pulsating flow of blood through the confronting surface. In turn, these volume changes cause momentary pressure changes within the earcup, which are generally inaudible low-frequency events correlated only to engagement of the earcup with surface 111. In response to these events, microphone 140 produces a low-frequency electrical signal which turn-off circuitry 130b monitors. If the turn-off circuitry detects that this signal is absent for a sufficient period of time, such as 2 or 3 or 5 or more minutes, it deactivates power switch 130c.

Figure 3:
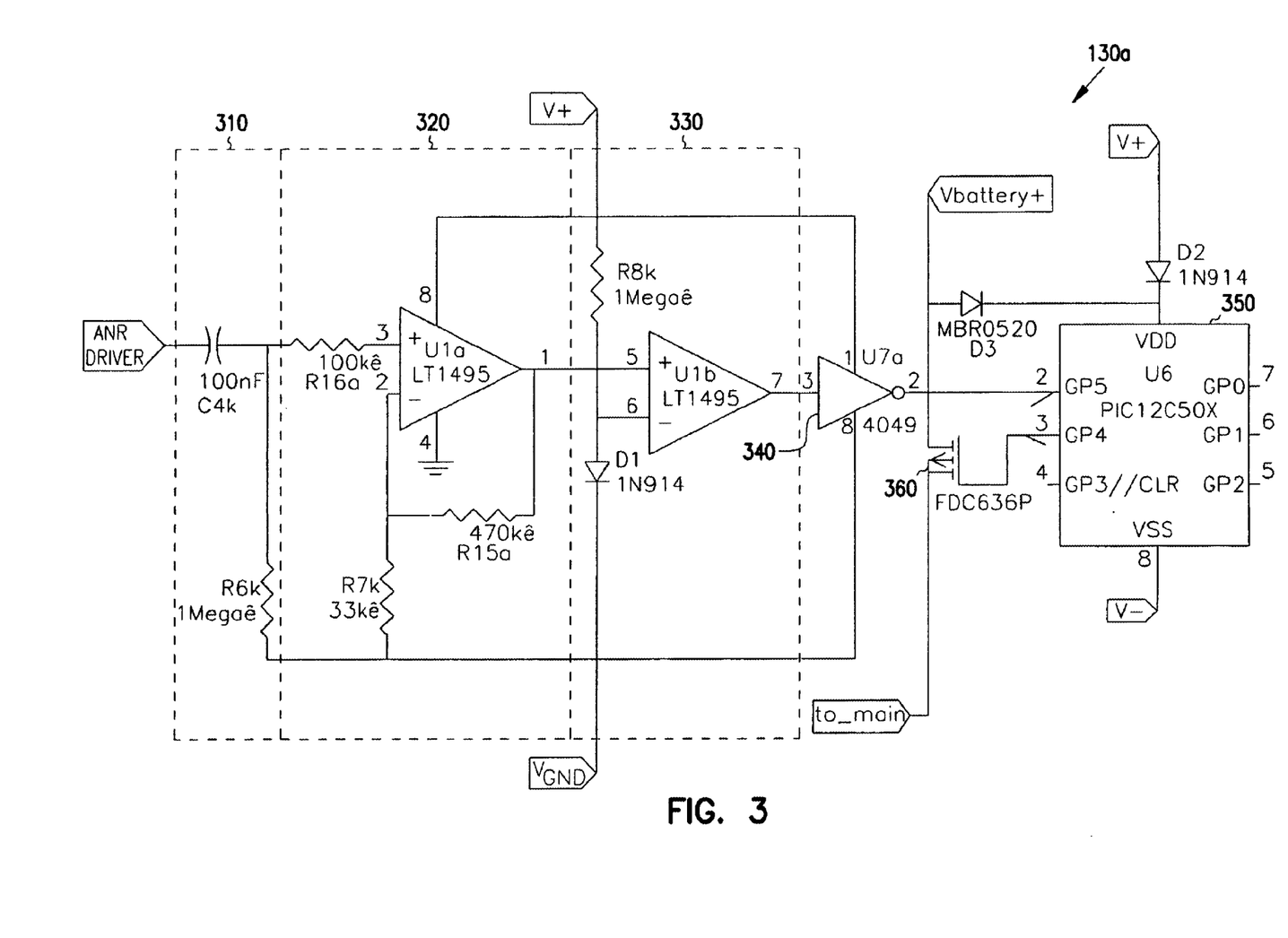
FIG. 3 is a schematic diagram of an exemplary turn-on circuit 300 incorporating the present invention.

FIG. 3 shows details of an exemplary embodiment of turn-on circuit 130a. In this embodiment, the turn-on circuit includes a high-pass filter 310, a preamplifier 320, threshold detector 330, an inverter 340, a processor 350, a switch 360, power supply terminals V+ and Vgnd, and a positive battery terminal Vbattery+. V+ and Vgnd are respectively +2.5 and zero volts in the exemplary embodiment. (Not shown in the diagram are one or more batteries, for example, AA batteries, and a switching regulator which provides the voltages of +2.5 and −2.5 volts.) In operation, turn-on circuitry draws on the order of 10 microamps from one or more supplied batteries. Hence, its impact on battery life is generally negligible.

More particularly, filter 310 comprises a 100-nanofarad capacitor C4k and a resistor R6k. Capacitor C4k has first and second terminals, with the first terminal coupled to the output of the ANR circuitry, or more precisely the ANR driver. The second terminal of capacitor C4k is coupled to ground via resistor R6k and to the input of preamplifier 320.

Preamplifier 320 comprises an LT1495 operational amplifier U1a, a one-mega-ohm resistor R6k, a 33 kilo-ohm resistor R7k, a 470-kilo-ohm resistor R15a, and 100-kilo-ohm input resistor R16a. Amplifier U1a has a negative and positive inputs and an output. The positive input is coupled via resistor R16a to a second terminal of capacitor C4k, and the negative input is coupled to terminal Vgnd via resistor R7k. Resistor R6k is coupled between the second terminal of capacitor C4k and ground, and resistor R15a is coupled between the output and the negative input of amplifier U1a. The output of amplifier U1a is coupled to the input of threshold detector 330.

Detector 330, which detects signals swings greater than 50 millivolts, includes an LT1495 operational amplifier U1b, a 1N914 diode D1, and a one-mega-ohm resistor R8k. Amplifier U1b has a positive input coupled to the output of amplifier U1a, and a negative input coupled to the positive terminal of diode D1. The negative terminal of diode D1 is coupled to ground, and resistor R8k is coupled between the positive terminal of diode D1 and positive supply terminal V+. Inverter 340 has its input coupled to the output of amplifier U1b, and its output coupled to an input of processor 350.

Processor 350 responds to an output signal indicating engagement of the headset with the user by activating switch 360. Activating switch 360, which in this embodiments comprises a p-channel mosfet transistor, connects power to the ANR circuitry enabling it to cancel or otherwise alter the acoustic energy within the earcup. A terminal of the mosfet is coupled to a shutdown pin of integrated switching regulator.

Figure 4:
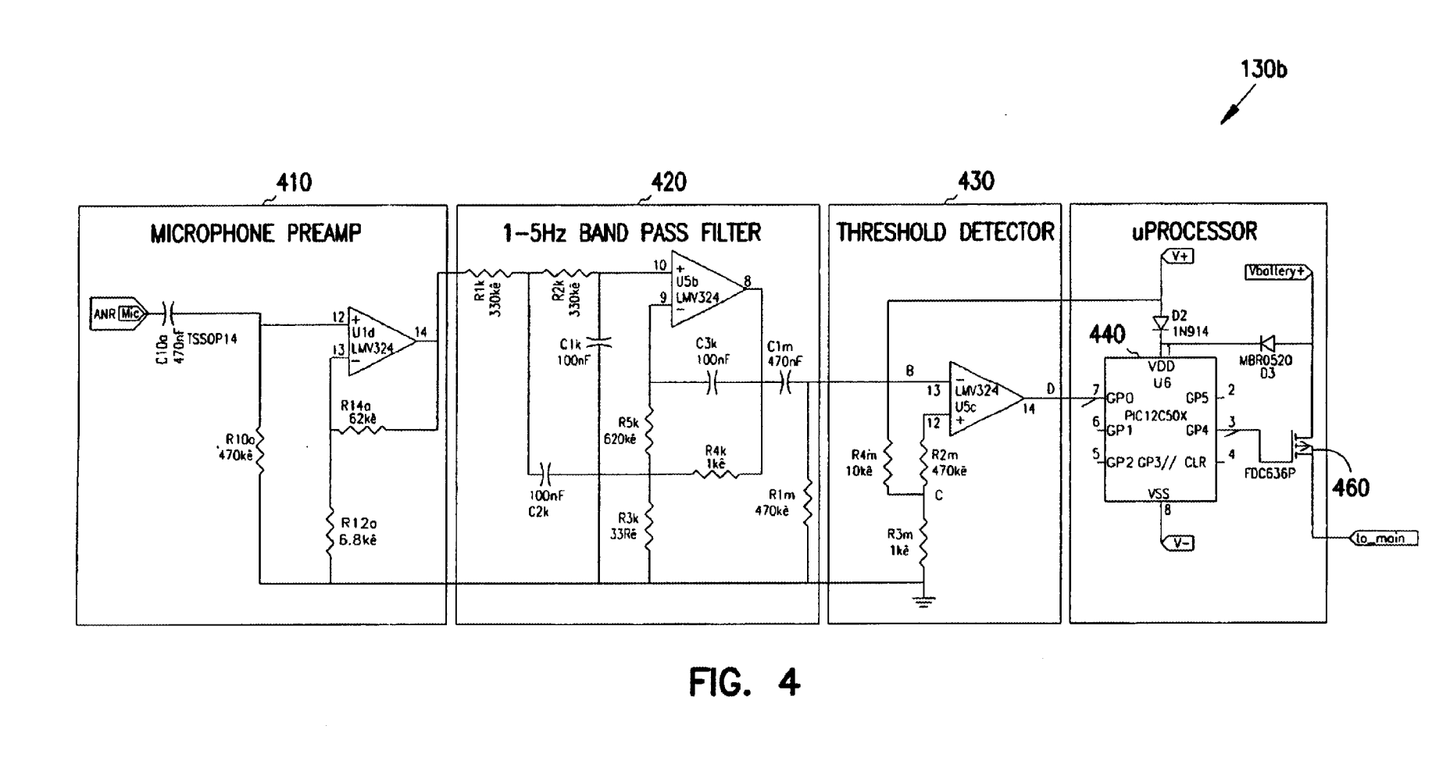
FIG. 4 is a schematic diagram of an exemplary turn-off circuit 400 incorporating the present invention.

FIG. 4 shows an exemplary embodiment of turn-off circuit 130b. Turn-off circuit 130b includes a microphone preamplifier 410, a bandpass filter 420, a threshold detector 430, a processor 450, a switch 460, respective positive and negative power-supply terminals V+ and V−, and a positive battery terminal (or node) Vbattery+. In the exemplary embodiment, terminals V+ and V− respectively provide 2.5 and −2.5 volts.

In operation, ANR microphone 140 senses pressure within earcup 120. When engaged with each other earcup 110 and surface 111 defines a substantially closed space with a volume that changes with user movements, such as head and jaw movements and the pulsating flow of blood through surface 111. In turn, these volume changes cause momentary pressure changes within the earcup, which are generally inaudible, low-frequency events. On the other hand, when disengaged from surface 111, earcup 110 is not pressed against surface 130 and thus no longer defines a volume subject to user movements. Thus, microphone 140 generally provides preamplifier 410 a signal with low-frequency content that changes during engagement of earcup 110 with surface 130 and that remains relatively constant after disengagement.

More particularly, preamplifier 410 has a gain of 20 decibels and comprises an input capacitor C10$a$ of 470 nanofarads, an input resistor R10$a$ of 470 kilo-ohms, an LMV324 operational amplifier U1$d$, and feedback resistors R12$a$ of 6.8 kilo-ohms and R14$a$ of 62 kilo-ohms. Amplifier U1$d$ provides an output signal proportional to the signal from preamplifier 410 to band-pass filter 420. (In some embodiment, preamplifier 410 also functions as a portion of ANR circuitry 150 (shown in FIG. 2).

Band-pass filter 420, which defines a one-to-five hertz passband with an approximate gain of 30 decibels, comprises a resistor R1$k$ of 330 kilo-ohms, a resistor R2$k$ of 330 kilo-ohms, a resistor R3$k$ of 33 kilo-ohms, a resistor R4$k$ of 1 kilo-ohm, a resistor R5$k$ of 620 kilo-ohms, and a resistor R1$m$ of 470 kilo-ohms. Filter 420 also comprises three 100-nanofarad capacitors C1$k$, C2$k$, and C3$k$, and one 470-nanofarad capacitor C1$m$. Filter 420 also comprises an operational amplifier U5$b$ which provides a pressure signal indicative of the pressure in earcup 120 via capacitor C1$m$ to threshold detector 430.

Threshold detector 430, which comprises an LMV324 operational amplifier, a 470-kilo-ohm resistor R2$m$, a 1-kiloohm resistor R3$m$, and a 10-kilo-ohm resistor R4$m$, compares the pressure signal to a 225-millivolt reference voltage at a node C and outputs a signal indicating the result of the comparison to processor 440. When the pressure signal at node B is greater than the reference voltage at node C, detector 430 outputs a low signal, which indicates an "on-head" event, that is, engagement of earcup 110 with surface 111, to processor 440.

In response to receiving an "on-head" event, processor 440 starts a timer which runs for a predetermined period of time, for example, two to three minutes. If during this period, another "on-head" event does not occur, that is, there are no sensed low-frequency events of sufficient magnitude, processor 440 assumes that the headset has been removed and sends an appropriate turn-off signal to a power-supply shutdown circuit, which turns off the headset. In some embodiments, processor 440 directly drives a shut-down pin on a switching regulator that provides the V+ and V−.supply voltages.

FIGS. 3 and 4 are shown as separate stand-alone circuits which are adaptable to virtually any active ANR headset to provide automatic mode control. When used together in the same headset, certain components of the circuits are shared to reduce the number of parts. For example, some embodiments use a single programmable processor and power switch. Moreover, some embodiments implement all or one or more portions of the circuit as an integrated circuit.

Figure 5:
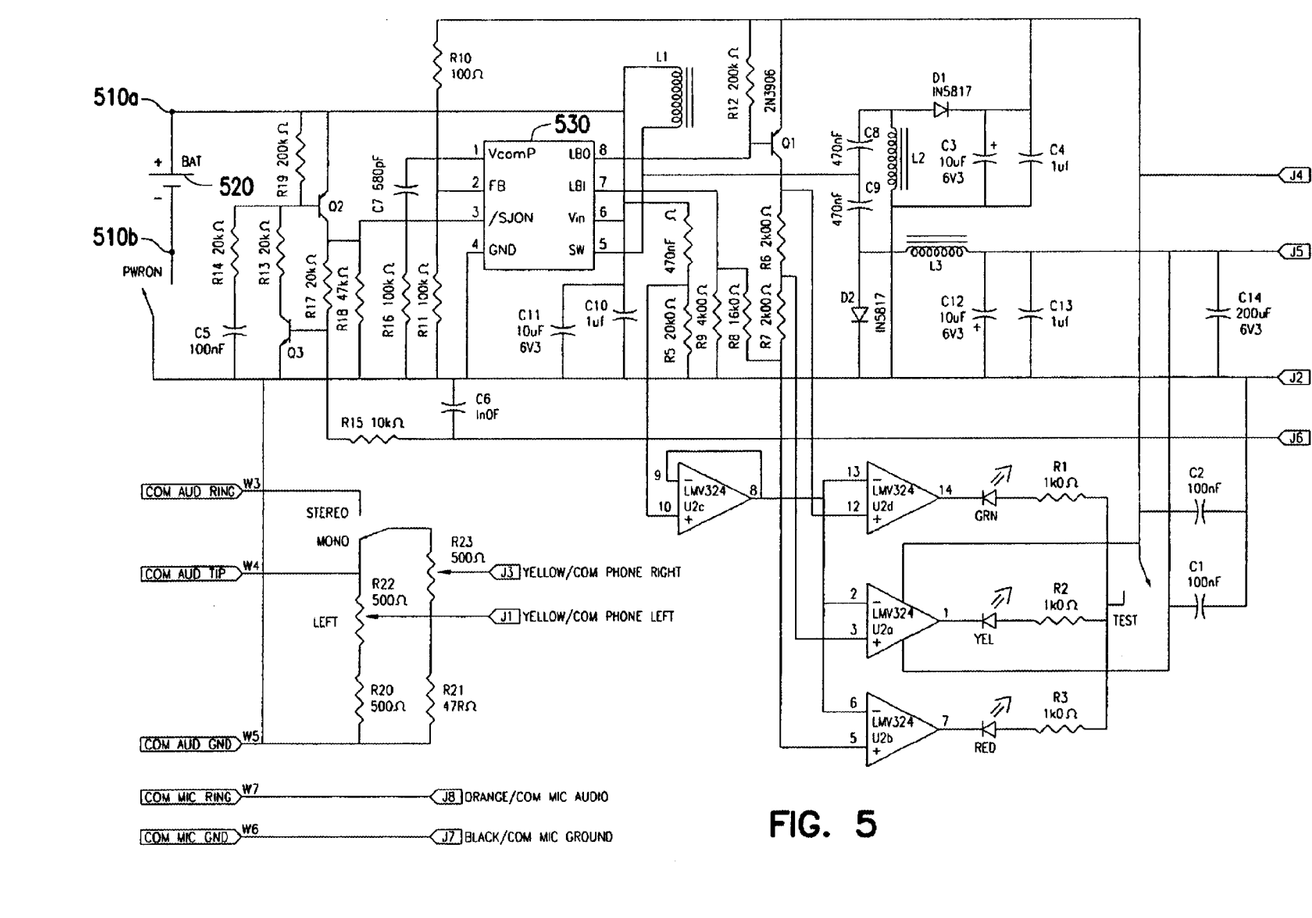
FIG. 5 is a schematic diagram of an exemplary power-supply circuit 500 for with turn-on circuit 300 and/or turn-on circuit 400.

FIG. 5 shows an exemplary embodiment of a power supply 500. Supply 500 includes, among other things, battery connection terminals 510$a$ and 510$b$, one or more batteries 520, and a integrated switching regulator circuit 530. Regulator circuit 530 includes a shutdown pin, which in the exemplary embodiment, ultimately coupled to a terminal of switch 360 or switch 460 in the turn-on and turn-off circuits of FIGS. 3 and 4. The present invention is not limited to any particular power supply arrangement.

Figure 6:
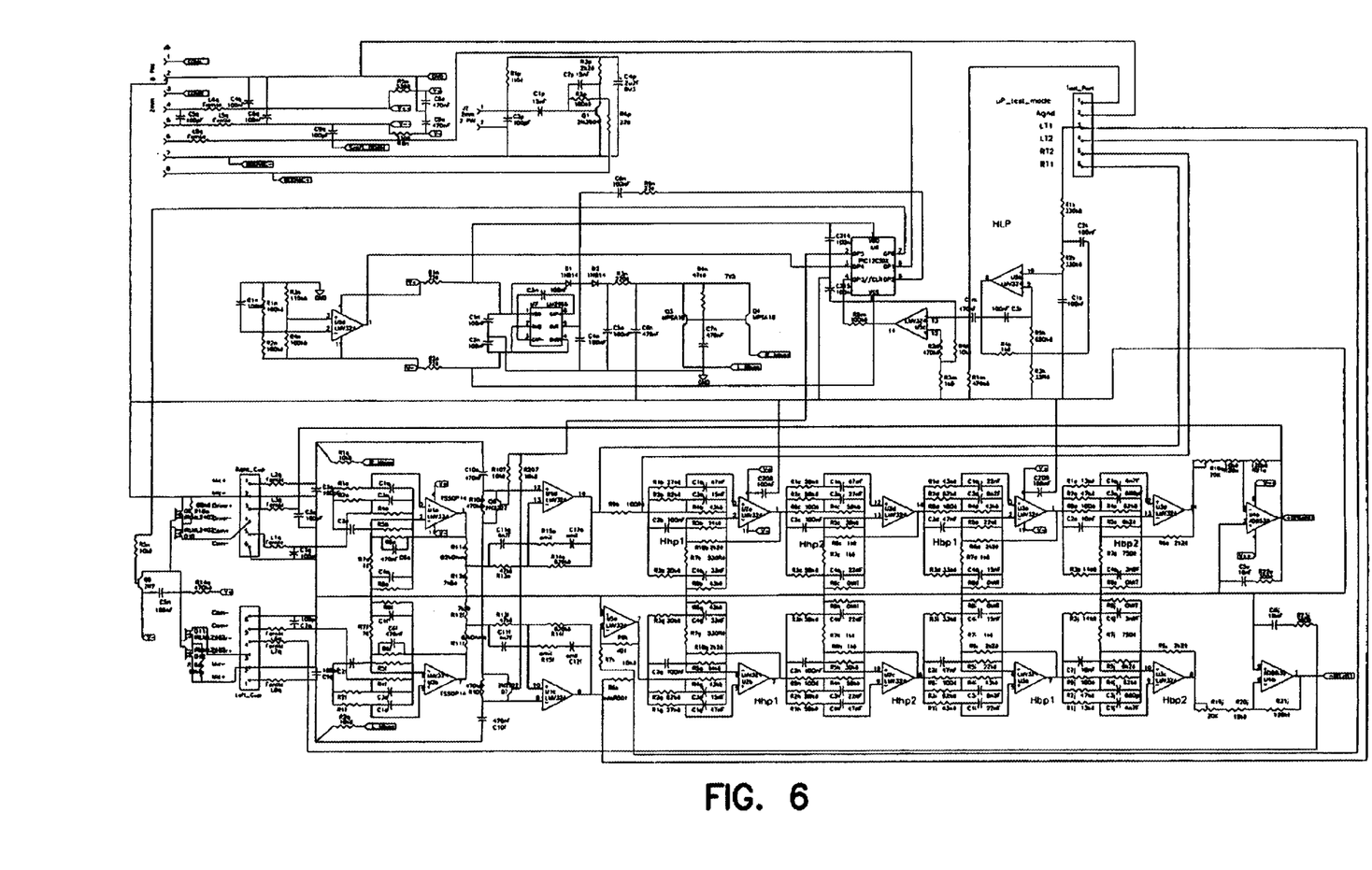
FIG. 6 is a schematic diagram of an exemplary headset 600 incorporating turn-off circuit 400 of FIG. 4.

FIG. 6 shows an exemplary embodiment of active headset 600 including a turn-off circuit in accord with the invention. FIG. 6 also shows details of an exemplary ANR circuitry.

Conclusion

In furtherance of the art, the inventor has presented one or more embodiments of active headsets incorporating an automatic mode control feature. One exemplary embodiment provides an turn-on and turn-off circuits which automatically detect engagement and disengagement of a headset to or from the head of a user to activate or deactivate the headset. The turn-off circuit is especially useful to conserve battery life in battery powered ANR headsets. However, the invention is generally applicable to automatically control the operational mode of any active headsets or headphones, regardless of the power source.

The embodiments described above are intended only to illustrate and teach one or more ways of practicing or implementing the present invention, not to restrict its breadth or scope. The actual scope of the invention, which encompasses all ways of practicing or implementing the concepts of the invention, is defined by the following claims and their equivalents.

What is claimed is:

1. An ANR headset having at least two operating states and comprising:

one or more earcups;

means for sensing a condition within at least one of the earcups, with the sensed condition being an inaudible condition based on user jaw movements or blood movement within a user's head; and means for changing the operating state of the headset from an on state to an off state in response to a perceived absence of the condition within the one earcup for at least a predetermined amount of time.

2. The headset of claim 1, wherein the predetermined period of time is at least one minute.

3. An ANR headset having at least two operating states and comprising:

one or more earcups;

means for sensing a condition within at least one of the earcups, wherein the sensed condition is an inaudible condition based on user jaw movements or blood movement and the means for sensing includes a first audio transducer within the one earcup; and means, coupled to the means for sensing a condition within the one earcup, for changing the operating state of the headset from an on state to an off state in response to a perceived absence of the condition for at least a predetermined period of time, wherein the means for changing the operating state includes a bandpass filter, a threshold detector, a processor, and a power switch, with the bandpass filter coupled between the threshold detector and the first audio transducer and the processor coupled between the threshold detector and the power switch.

4. The headset of claim 3, wherein the means for changing the operating state of the headset changes the operating state from the on state to the off state in response to perceived absence of the condition for at least one minute.

5. The headset of claim 1 further including means for changing the operating state of the headset from the off state to the on state.

6. The headset of claim 1, wherein the one earcup engages the head of a user to define a volume and the means for sensing senses changes of the volume.

7. An ANR headset having at least an active operating state and an inactive operating state and comprising:

one or more earcups;

an ANR microphone for sensing a condition within at least one of the earcups, with the sensed condition being an inaudible condition based on user jaw movements or blood movement within the user's head;

a timer circuit for measuring duration of a perceived absence of the condition for at least a predetermined amount of time; and a switch coupled to the timer circuit for switching the ANR headset from one of the active and inactive operating states to the other of the active and inactive operating states after the perceived absence for at least the predetermined amount of time.

8. The ANR headset of claim 7, wherein the timer circuit comprises:

a threshold detector; and a microprocessor coupled to the threshold detector for operating the switch.

9. The ANR headset of claim 7, wherein the predetermined amount of time is at least one minute.

10. A method of operating an ANR headset including an audio transducer attached to an earcup for engaging the ear of a user, the method comprising:

sensing a condition within a cavity at least partly defined upon engagement of the earcup with the ear of a user, with the sensed condition being an inaudible condition based on user jaw movement or blood flow in a user's head; and switching at least a portion of ANR headset from an active state to an inactive state in response to a perceived absence of the condition for at least a predetermined amount of time.

11. A method of claim 10, wherein switching at least the portion of the ANR headset comprises switching in response to sensing an absence of certain frequency content from the output of an audio transducer within a cavity for an amount of time of at least one minute.

12. The method of claim 10, wherein the ANR headset includes an ANR driver within the cavity and ANR circuitry coupled to the ANR driver; and wherein the method further comprises switching the ANR circuitry from the inactive state to the active state in response to sensing deflection of a portion of the ANR driver.

13. The method of claim 11, wherein the certain frequency content is no greater than 5 Hertz.

* * * * *